United States Patent
Hirokawa et al.

(10) Patent No.: US 11,871,991 B2
(45) Date of Patent: Jan. 16, 2024

(54) IMAGE PROCESSING METHOD, PROGRAM, AND IMAGE PROCESSING DEVICE

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 17/072,346

(22) Filed: Oct. 16, 2020

(65) Prior Publication Data

US 2021/0030266 A1 Feb. 4, 2021

Related U.S. Application Data

(63) Continuation of application No. PCT/JP2019/016655, filed on Apr. 18, 2019.

(30) Foreign Application Priority Data

Apr. 18, 2018 (JP) ................................ 2018-080276

(51) Int. Cl.
| | |
|---|---|
| *G06T 7/33* | (2017.01) |
| *G06T 7/246* | (2017.01) |
| *A61B 3/12* | (2006.01) |
| *G06T 11/20* | (2006.01) |
| *A61B 3/00* | (2006.01) |
| *G06T 5/00* | (2006.01) |

(Continued)

(52) U.S. Cl.
CPC .......... *A61B 3/0025* (2013.01); *A61B 3/0058* (2013.01); *A61B 3/1241* (2013.01); *G06T 5/007* (2013.01); *G06T 7/0016* (2013.01); *G06T 7/248* (2017.01); *G06T 7/33* (2017.01); *G06T 11/001* (2013.01); *G06T 11/206* (2013.01); *G06T 2207/10016* (2013.01); *G06T 2207/30041* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 10,987,010 B2* | 4/2021 | Grady | ................. A61B 5/7275 |
| 2004/0142485 A1 | 7/2004 | Flower | |

(Continued)

FOREIGN PATENT DOCUMENTS

| | | |
|---|---|---|
| EP | 3300654 A2 | 4/2018 |
| JP | H11-70081 A | 3/1999 |

(Continued)

OTHER PUBLICATIONS

Office Action issued in corresponding Japanese Patent Application No. 2020-514439 dated Feb. 14, 2023 (10 pages).

(Continued)

*Primary Examiner* — James A Thompson
(74) *Attorney, Agent, or Firm* — Foley & Lardner LLP

(57) ABSTRACT

Data is computed in order to visualize the velocity of blood fluid flowing through a blood vessel at a fundus. An image processing method includes a step of performing registration of each frame in a moving image configured by plural frames of an imaged fundus, and a step of computing visualization data enabling visualization of a state of blood fluid flowing through a blood vessel at the fundus based on a pixel value in each of the registered frames.

22 Claims, 8 Drawing Sheets

(51) Int. Cl.
    *G06T 7/00*    (2017.01)
    *G06T 11/00*   (2006.01)

(56)        References Cited

U.S. PATENT DOCUMENTS

2011/0190633 A1     8/2011   Kawagishi et al.
2014/0354794 A1*   12/2014   Imamura .............. A61B 5/0285
                                                          348/78
2015/0206308 A1     7/2015   Nempont et al.
2016/0022236 A1     1/2016   Ohishi
2018/0064576 A1*    3/2018   Chen ..................... A61B 3/113
2018/0070814 A1*    3/2018   Mikaelian .............. A61B 3/024

FOREIGN PATENT DOCUMENTS

JP      2010-246725 A    11/2010
JP      2011-177494 A     9/2011
JP      2015-519987 A     7/2015

OTHER PUBLICATIONS

Office Action issued in corresponding Japanese Patent Application No. 2020-514439, dated Jul. 4, 2023 (10 pages).

* cited by examiner

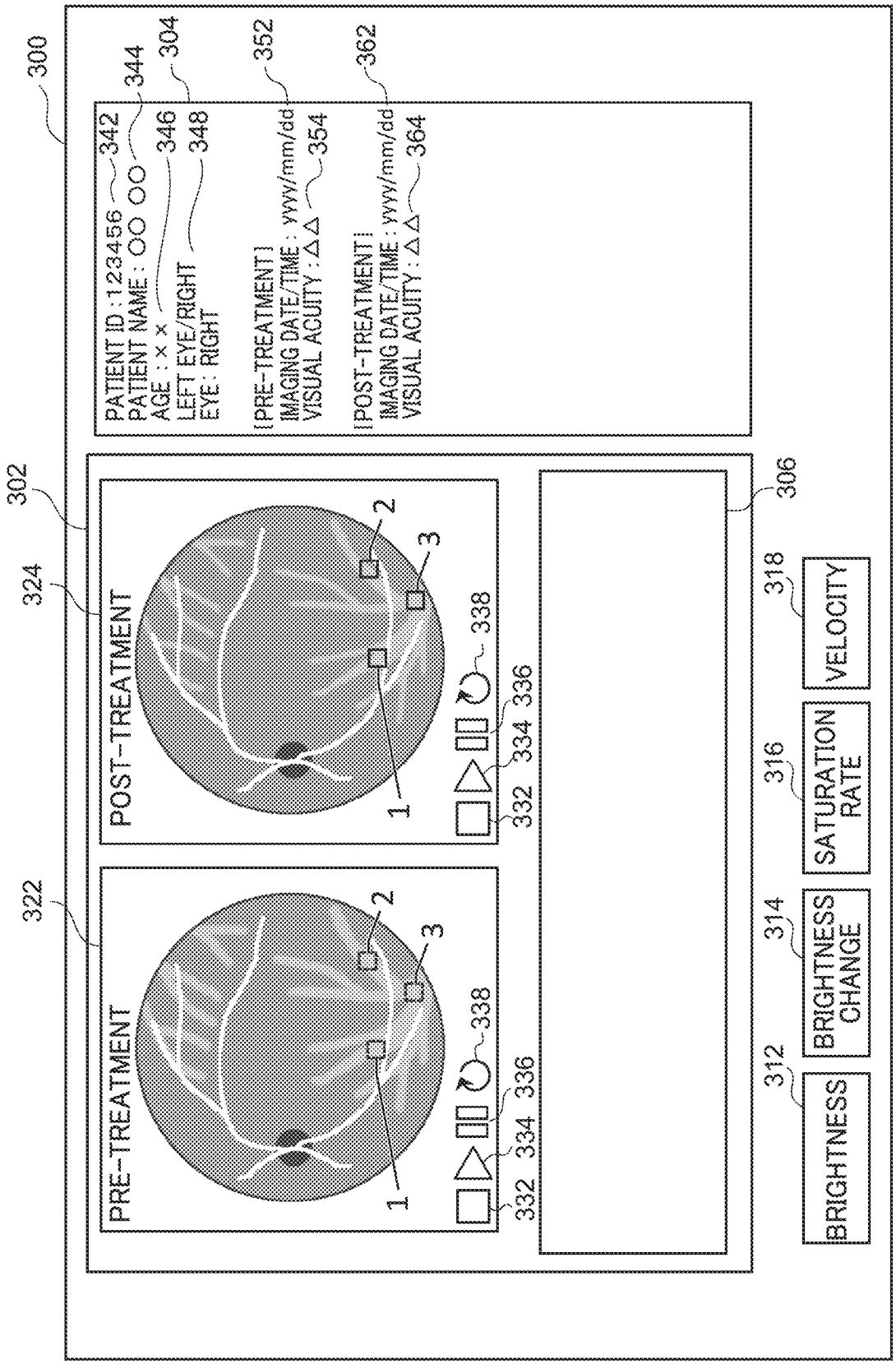

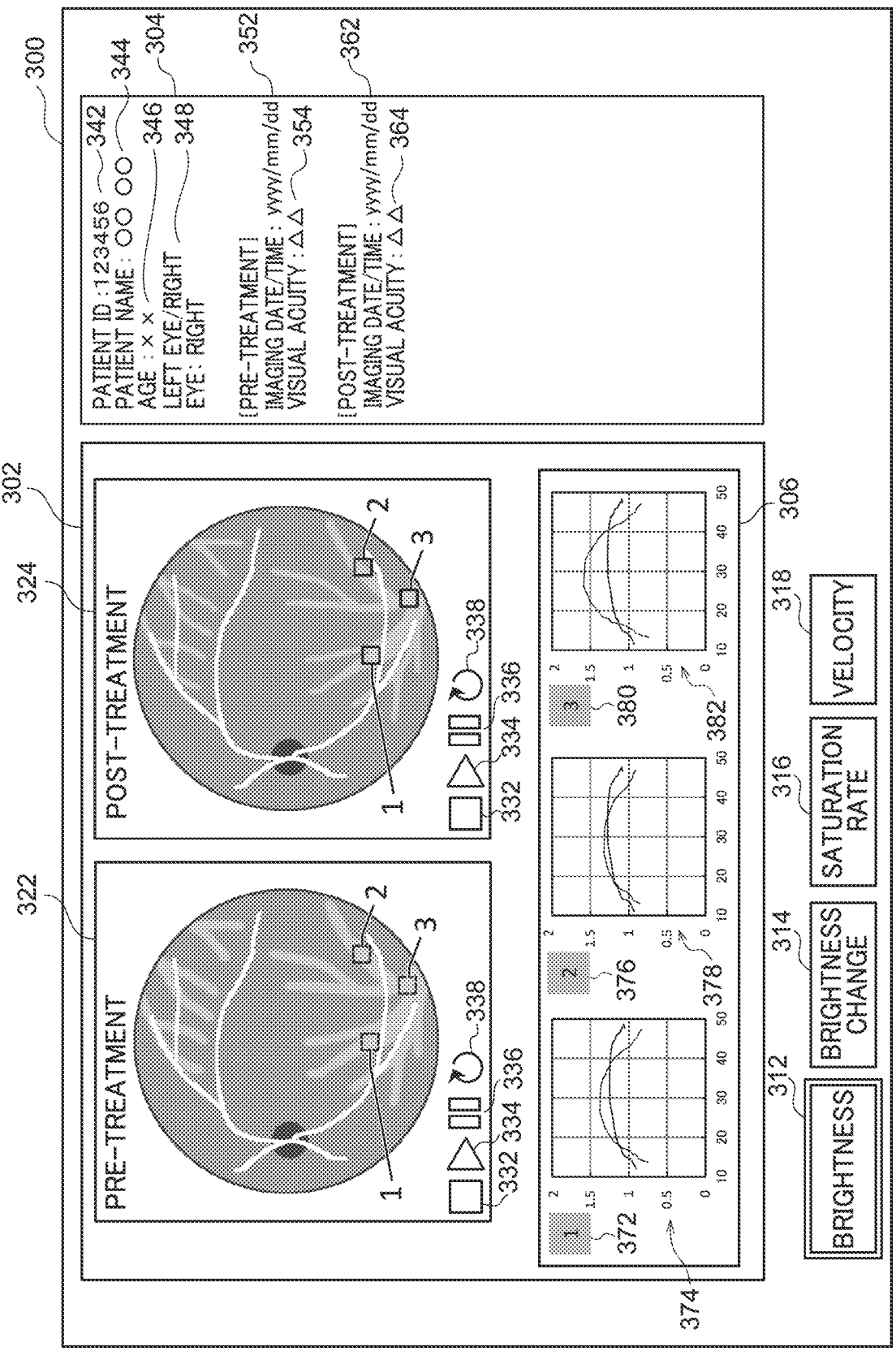

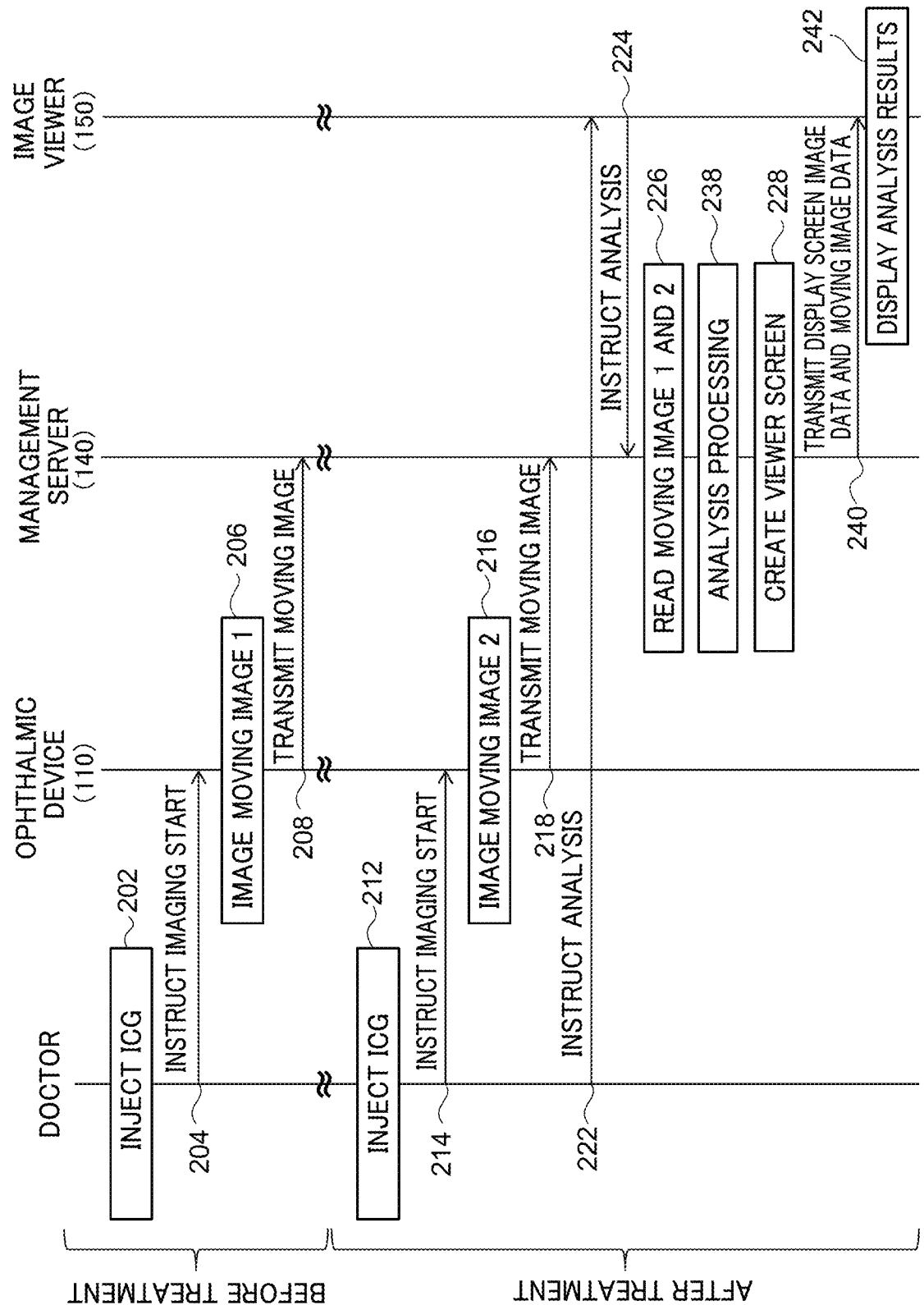

IMAGE PROCESSING METHOD, PROGRAM, AND IMAGE PROCESSING DEVICE

CROSS-REFERENCE TO RELATED APPLICATIONS

This application is a continuation application of International Application No. PCT/JP2019/016655 filed Apr. 18, 2019, the disclosure of which is incorporated herein by reference in its entirety. Further, this application claims priority from Japanese Patent Application No. 2018-080276, filed Apr. 18, 2018, the disclosure of which is incorporated herein by reference in its entirety.

TECHNICAL FIELD

Technology disclosed herein relates to an image processing method, a program, and an image processing device.

RELATED ART

US Patent Application Publication No. 2004/0142485 discloses technology to control display of an angiographic image.

SUMMARY

An image processing method of a first aspect of technology disclosed herein includes a step of performing registration of an image of each frame in a moving image including plural frame images of a fundus, and a step of computing data enabling visualization of a velocity of blood fluid flowing through a blood vessel at the fundus based on plural pixel values in each of the registered frame images.

A program of a second aspect of technology disclosed herein causes a computer to execute the image processing method of the first aspect.

An image processing device of a third aspect of technology disclosed herein includes a storage device configured to store a program for causing a processing device to execute an image processing method, and a processing device configured to execute the image processing method by executing the program stored in the storage device. The image processing method is the image processing method of the first aspect.

An image processing method of a fourth aspect of technology disclosed herein includes a step of performing registration of each frame in a first moving image configured by plural first frames of an imaged fundus, a step of performing registration of each frame in a second moving image configured by plural second frames of the imaged fundus, a step of computing first visualization data enabling visualization of a state of blood fluid flowing through a blood vessel at the fundus based on a pixel value in the plural registered first frames, and a step of computing second visualization data enabling visualization of a state of blood fluid flowing through the blood vessel at the fundus based on a pixel value in the plural registered second frames.

BRIEF DESCRIPTION OF DRAWINGS

FIG. 7 is a diagram illustrating a viewer screen 300 of an image viewer 150.
FIG. 8 is a diagram illustrating a viewer screen (analysis results display screen) 300 of the image viewer 150.
FIG. 9 is a sequence chart illustrating operation of an ophthalmic system 100 before and after treatment by a doctor in a third modified example.

DETAILED DESCRIPTION

Detailed explanation follows regarding exemplary embodiments of the present invention, with reference to the drawings. In the following, for ease of explanation, a scanning laser ophthalmoscope is referred to as an "SLO".

Figure 1:
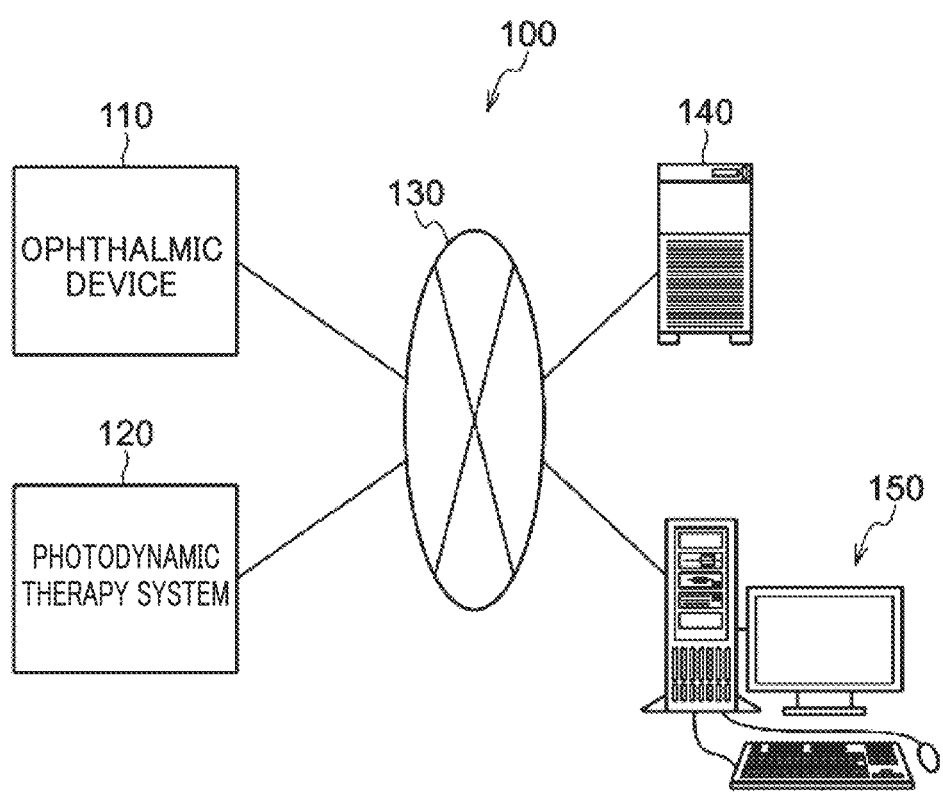
FIG. 1 is a block diagram of an ophthalmic system 100.

The configuration of an ophthalmic system 100 will be now described with reference to FIG. 1. As shown in FIG. 1, the ophthalmic system 100 includes an ophthalmic device 110, a photodynamic therapy system 120, a management server device (hereinafter referred to as "management server") 140, and an image display device (hereinafter referred to as "image viewer") 150. The ophthalmic device 110 acquires fundus images. The photodynamic therapy system 120 performs photodynamic therapy (PDT) on an examined eye of a patient. The management server 140 stores plural fundus images and eye axial lengths obtained by imaging the fundi of plural patients using the ophthalmic device 110 in association with respective patient IDs. The image viewer 150 displays fundus images acquired by the management server 140.

Icons and buttons for instructing image generation, described later, are displayed on the display screen of the image viewer 150, also described later. When an ophthalmologist clicks on one of the icons etc., an instruction signal corresponding to the clicked icon etc. is transmitted from the image viewer 150 to the management server 140. On receipt of the instruction signal from the image viewer 150, the management server 140 generates an image in accordance with the instruction signal, and transmits image data of the generated image to the image viewer 150. The image viewer 150 that has received the image data from the management server 140 then displays an image based on the received image data on a display. Display screen generation processing is performed in the management server 140 by the CPU 162 executing a display screen generation program.

The ophthalmic device 110, the photodynamic therapy system 120, the management server 140, and the image viewer 150 are connected to each other over a network 130.

Note that other ophthalmic instruments (instruments for tests such as field of view measurement and intraocular pressure measurement) and a diagnostic support device that performs image analysis using artificial intelligence may be connected to the ophthalmic device 110, the photodynamic therapy system 120, the management server 140 and the image viewer 150 over the network 130.

Figure 2:
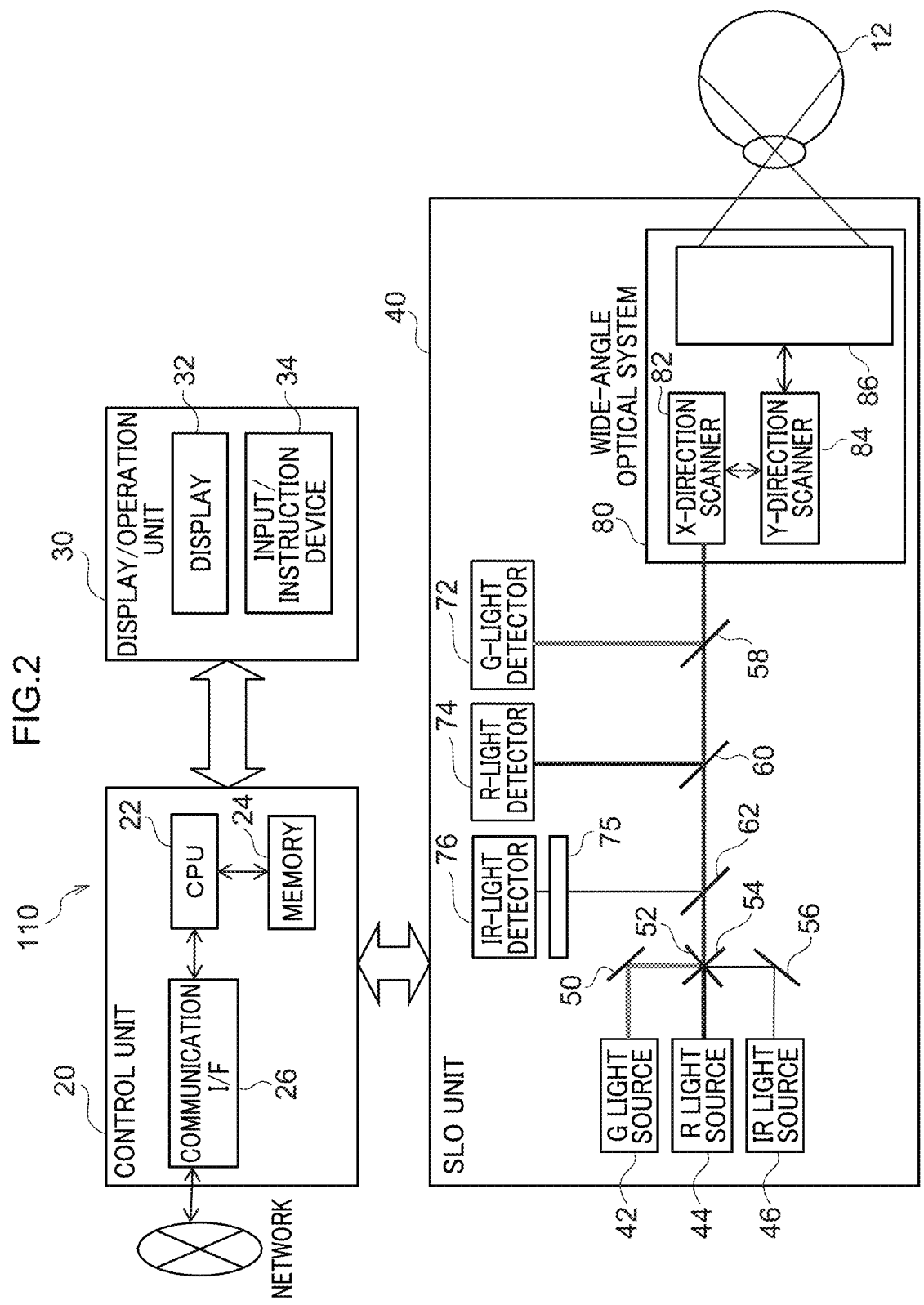
FIG. 2 is a schematic configuration diagram illustrating an overall configuration of an ophthalmic device 110.

Explanation follows regarding a configuration of the ophthalmic device 110, with reference to FIG. 2. As shown in FIG. 2, the ophthalmic device 110 includes a control unit 20, a display/operation unit 30, and an SLO unit 40, and images the posterior eye portion (fundus) of the examined eye 12. Furthermore, a non-illustrated OCT unit may be provided for acquiring OCT data of the fundus.

The control unit 20 includes a CPU 22, memory 24, a communication interface (I/F) 26, and the like. The display/operation unit 30 is a graphical user interface that displays an image obtained by imaging and accepts various instructions including an imaging instruction. The display/operation unit 30 includes a display 32 and an input/instruction device 34.

The SLO unit 40 includes a light source 42 for green light (G-light: wavelength 530 nm), a light source 44 for red light (R-light: wavelength 650 nm), and a light source 46 for infrared radiation (IR-light (near-infrared light): wavelength 800 nm). The light sources 42, 44, 46 respectively emit light as commanded by the control unit 20. Visible light having a wavelength of 630 nm to 780 nm is used as the R-light light source, and a laser light source that emits near-infrared light having a wavelength of 780 nm or more is used as the IR-light light source.

The SLO unit 40 includes optical systems 50, 52, 54 and 56 that reflect or transmit light from the light sources 42, 44 and 46 in order to guide the reflected light into a single optical path. The optical systems 50 and 56 are mirrors, and the optical systems 52 and 54 are beam splitters. The G-light is reflected by the optical systems 50 and 54, the R-light is transmitted through the optical systems 52 and 54, and the IR-light is reflected by the optical systems 52 and 56, such that all are guided into a single optical path.

The SLO unit 40 includes a wide-angle optical system 80 for two-dimensionally scanning light from the light sources 42, 44, 46 over the posterior eye portion (fundus) of the examined eye 12. The SLO unit 40 includes a beam splitter 58 that, from out of the light from the posterior eye portion (fundus) of the examined eye 12, reflects the G-light and transmits light other than the G-light. The SLO unit 40 includes a beam splitter 60 that, from out of the light transmitted through the beam splitter 58, reflects the R-light and transmits light other than the R-light. The SLO unit 40 includes a beam splitter 62 that, from out of the light that has passed through the beam splitter 60, reflects IR-light. The SLO unit 40 is provided with a G-light detection element 72 that detects the G-light reflected by the beam splitter 58, an R-light detection element 74 that detects the R-light reflected by the beam splitter 60, and an IR-light detection element 76 that detects IR-light reflected by the beam splitter 62.

An optical filter 75 is provided between the beam splitter 62 and the IR-light detection element 76, for example in the vicinity of a region where light is incident to the IR-light detection element 76. A surface of the optical filter 75 has a surface area covering this entire region. The optical filter 75 is moved by a non-illustrated moving mechanism under control by the CPU 22 between a position where the surface of the optical filter 75 covers the entire region and a position where the surface of the optical filter 75 does not cover the entire region. The optical filter 75 is a filter that blocks the IR-light (wavelength 780 nm) emitted from the IR light source 46 while allowing fluorescent light (wavelength 330 nm) generated by ICG, described later, to pass through.

The wide-angle optical system 80 includes an X-direction scanning device 82 configured by a polygon mirror to scan the light from the light sources 42, 44, 46 in an X direction, a Y-direction scanning device 84 configured by a galvanometer mirror to scan the light from the light sources 42, 44, 46 in a Y direction, and an optical system 86 including a non-illustrated slit mirror and elliptical mirror to widen the angle over which the light is scanned. The optical, system 86 is capable of achieving a field of view (FOV) of the fundus with a larger angle than in conventional technology, enabling a fundus region to be imaged over a wider range than when employing conventional technology. More specifically, a fundus region can be imaged over a wide range of approximately 120 degrees of external light illumination angles from outside the examined eye 12 (in practice approximately 200 degrees about a center O of the eyeball of the examined eye 12 as a reference position for an internal light illumination angle capable of being imaged by illuminating the fundus of the examined eye 12 with scanning light). The optical system 86 may be configured employing plural lens sets instead of a slit mirror and elliptical mirror. The X-direction scanning device 82 and the Y-direction scanning device 84 may also be scanning devices employing two-dimensional scanners configured by MEMS mirrors.

A system using an elliptical mirror as described in International Applications PCT/JP2014/084619 or PCT/JP2014/084630 may be used in cases in which a system including a slit mirror and an elliptical mirror is used as the optical system 86. The respective disclosures of International Application PCT/JP2014/084619 (International Publication WO2016/103484) filed on Dec. 26, 2014 and International Application PCT/JP2014/084630 (International Publication WO2016/103489) filed on Dec. 26, 2014 are incorporated by reference herein in their entireties.

Note that when the ophthalmic device 110 is installed on a horizontal plane, the "X direction" corresponds to a horizontal direction and the "Y direction" corresponds to a direction perpendicular to the horizontal plane. A direction connecting the center of the pupil of the anterior eye portion of the examined eye 12 and the center of the eyeball is referred to as the "Z direction". The X direction, the Y direction, and the Z direction are accordingly perpendicular to one another.

The photodynamic therapy system 120 in FIG. 1 is a system that illuminates a pathological lesion on the fundus with a weak laser beam after internal administration of a light-responsive drug to perform PDT. PDT is performed to treat age-related macular degeneration and central serous chorioretinopathy.

Figure 3:
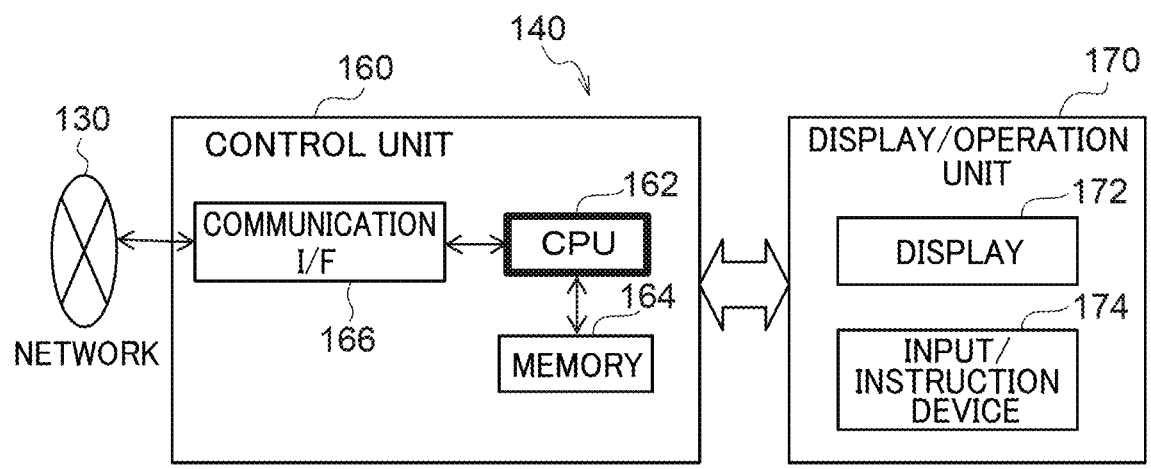
FIG. 3 is a block diagram illustrating a configuration of an electrical system of a management server 140.

Next, explanation follows regarding a configuration of the management server 140, with reference to FIG. 3. As illustrated in FIG. 3, the management server 140 includes a control unit 160, and a display/operation unit 170. The control unit 160 includes a computer including a CPU 162, memory 164 configured by a storage device, a communication interface (I/F) 166, and the like. An analysis processing program is stored in the memory 164. The display/operation unit 170 is a graphical user interface for displaying images and for accepting various instructions. The display/operation unit 170 includes a display 172 and an input/instruction device 174 such as a touch panel.

A configuration of the image viewer 150 is similar to that of the management server 140, and explanation thereof will be omitted.

Figure 4:
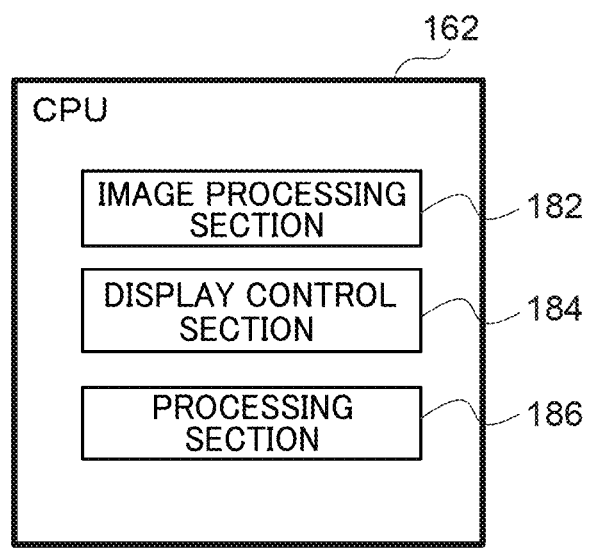
FIG. 4 is a functional block diagram of a CPU 162 of the management server 140

Next, explanation follows regarding each of various functions implemented by the CPU 162 of the management server 140 executing the analysis processing program, with reference to FIG. 4. The analysis processing program includes an analysis processing function, a display control function, and a processing function. By the CPU 162 executing the analysis processing program including each of these functions, the CPU 162 functions as an image processing section 182, a display control section 184, and a processing section 186, as illustrated in FIG. 4.

Figure 5:
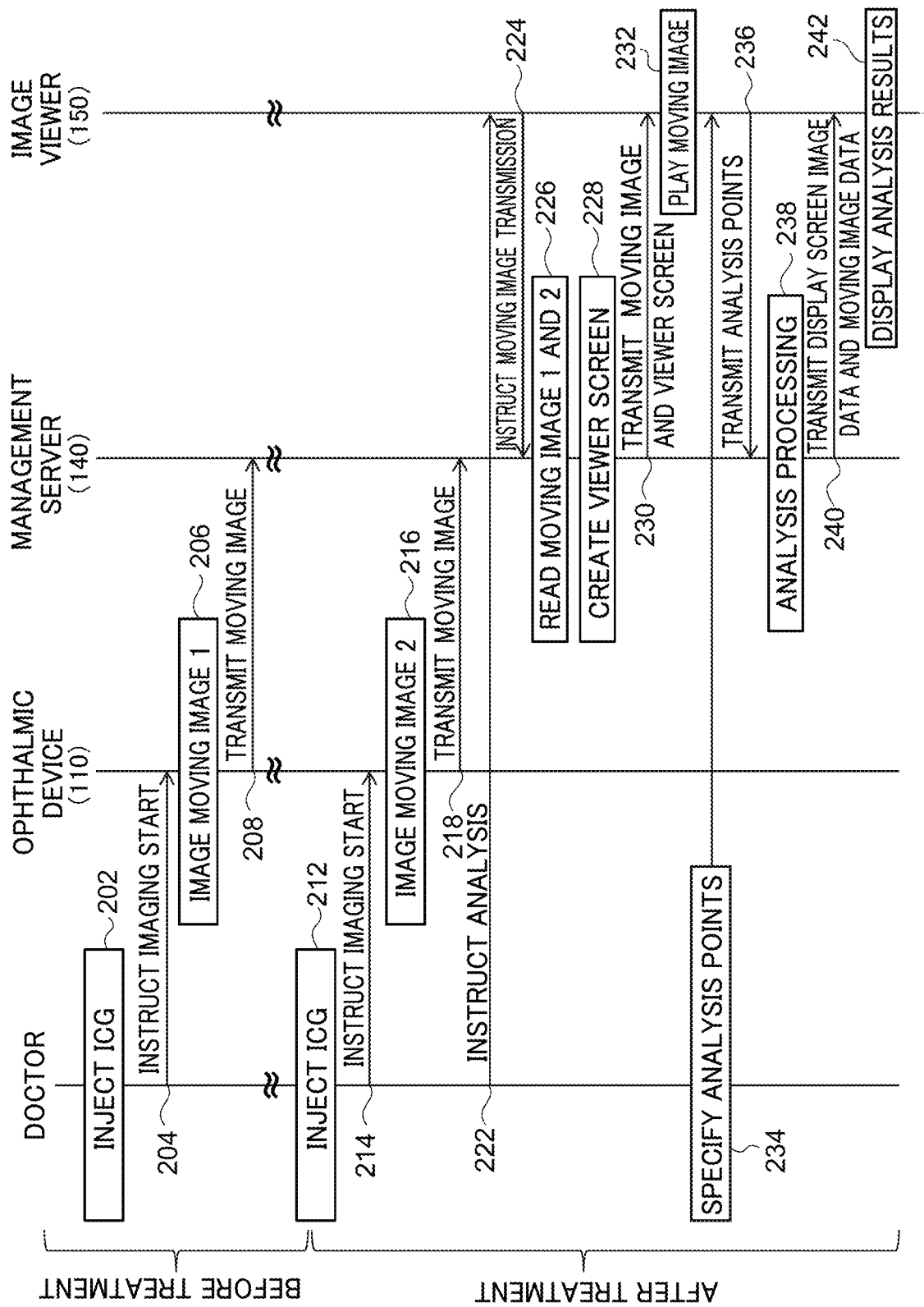
FIG. 5 is a sequence chart illustrating operation of the ophthalmic system 100 before and after treatment by a doctor.

Next explanation follows, with reference to FIG. 5, regarding use of the photodynamic therapy system 120, and operation of the ophthalmic system 100, to produce a visualization of a state of blood flow in choroidal blood vessels before and after treatment by a doctor of, for example, age-related macular degeneration disease or central serous chorioretinopathy.

Imaging of the examined eye of a patient is performed using the photodynamic therapy system 120 before treating the examined eye using PDT. A specific example of this is described below.

The examined eye of the patient is positioned so as to allow imaging of the examined eye of the patient using the ophthalmic device 110. As illustrated in FIG. 5, at step 202, the doctor administers a fluorescent dye (contrast agent, indocyanine green (hereinafter, referred to as "ICG")) into the body by intravenous injection. ICG is used to examine vascular lesions of the choroid since the excitation wavelength of ICG and the wavelength of fluorescent light therefrom are both in the near-infrared region. At step 204, the ophthalmic device 110 is instructed via the input/instruction device 34 to start ICG fluorescence fundus imaging. At step 206 the ophthalmic device 110 starts ICG fluorescence fundus imaging using the SLO unit 40 (moving image 1 imaging). Specifically, the control unit 20 of the ophthalmic device 110 controls the IR light source 46 and the IR-light detection element 76 of the SLO unit 40 so as to image the fundus of the examined eye at a frequency of N (natural number) times per second for a specific period of time T (natural number) seconds. Moving image data is accordingly generated for the moving image 1 by imaging the fundus of the examined eye for the specific period of time T at N frames per second. Thus N×T image frames are obtained as the moving image 1. For example, N×T=10×60=600 image frames are obtained.

When ICG has been intravenously injected, the ICG starts to flow through the blood vessels of the fundus after a fixed period of time has elapsed. When this occurs the ICG is excited by the IR-light (780 nm) from the IR light source 46, and fluorescent light having a wavelength (830 nm) in the near-infrared region is generated by the ICG. Moreover, when imaging the fundus of the examined eye (step 206) to generate the moving image data of moving image 1, the optical filter 75 (see FIG. 2) is inserted in the vicinity of and in front of the region where light is incident onto the IR-light detection element 76. As described above, the optical filter 75 blocks IR light (wavelength 780 nm) emitted from the IR light source 46 while allowing the fluorescent light emitted from the ICG (wavelength 830 nm) to pass through. This means that only the fluorescent light emitted from the ICG is received by the IR-light detection element 76, enabling ICG fluorescence fundus imaging (moving image 1 imaging) to be performed, and producing a visualization of the blood flowing along with the ICG.

When imaging of the moving image 1 (imaging of the examined eye for the specific period of time) has been completed, at the next step 208 the ophthalmic device 110 transmits the moving images (N×T frames) obtained by imaging of the moving image 1 to the management server 140.

After step 208, the photodynamic therapy system 120 performs PDT on a specified site in the examined eye of the patient (pathological lesion) so as to treat the examined eye.

After treating the examined eye (for example, after 3 months have elapsed), imaging of the examined eye is performed again to confirm the efficacy of the treatment. This is specifically performed as follows.

The examined eye of the patient is positioned so as to enable imaging of the patient's examined eye using the ophthalmic device 110. At step 212, the doctor administers ICG into the body by intravenous injection, and at step 214 the doctor instructs the ophthalmic device 110 to start imaging via the input/instruction device 34. At step 216 the ophthalmic device 110 performs imaging of a moving image 2. Note that since imaging of the moving image 2 at step 216 is similar to the imaging of the moving image 1 at step 206 explanation thereof will be omitted. At step 218, the ophthalmic device 110 transmits the moving images obtained by imaging the moving image 2 (N×T frames) to the management server 140.

When imaging the moving image 1 at step 206 and when imaging the moving image 2 at step 216, various information, such as a patient ID, patient name, age, information as to whether each image is from the right or left eye, the date/time of imaging and visual acuity before treatment, and the date/time of imaging and visual acuity after treatment, is also input to the ophthalmic device 110. The various information described above is transmitted from the ophthalmic device 110 to the management server 140 when the moving images are transmitted at step 208 and step 218.

At step 222, the user of the image viewer 150 (an ophthalmologist or the like) instructs the image viewer 150 to perform analysis processing via the input/instruction device 174 of the image viewer 150.

At step 224, the image viewer 150 instructs the management server 140 to transmit the corresponding moving images. When instructed to transmit the moving images, at step 226 the management server 140 reads the moving images 1, 2 and at step 228 creates a viewer screen.

Explanation follows regarding the viewer screen. FIG. 7 illustrates a viewer screen 300. As illustrated in FIG. 7, the viewer screen 300 includes an image display region 302, and a patient information display region 304. A brightness information display instruction icon 312, a brightness change information display instruction icon 314, a saturation rate display instruction icon 316, and a velocity display instruction icon 318 are displayed on the viewer screen 300.

A pre-treatment image display region 322 to display an image (the moving image 1) from before treatment, a post-treatment image display region 324 to display an image (the moving image 2) from after treatment, and an information display region 306 are provided in the image display region 302.

A stop icon 332 to instruct stopping of image (moving image 1) playback, a play icon 334 to instruct image playback, a pause icon 336 to instruct pausing of image playback, and a repeat icon 338 to instruct repeat of image playback are provided in the pre-treatment image display region 322. Note that icons from the stop icon 332 to the repeat icon 338 are also provided in the post-treatment image display region 324.

A patient ID display region 342, a patient name display region 344, an age display region 346, a display region 348 to display information (left or right) to indicate whether each image is from the left eye or the right eye, a pre-treatment imaging date/time display region 352, a pre-treatment visual acuity display region 354, a post-treatment imaging date/time display region 362, and a post-treatment visual acuity display region 364 are provided in the patient information display region 304.

When the viewer screen 300 has been created, at step 230 the management server 140 transmits the data of the moving images 1, 2 and the viewer screen 300 to the image viewer 150. At step 232 the image viewer 150 plays the moving images 1, 2.

At step 234, the user (ophthalmologist or the like) operates the viewer screen 300 to specify analysis points. Specification of the analysis points is specifically performed in the following manner.

An image of a specific frame of the pre-treatment moving image 1, for example, the final frame therein, is displayed in the image display region 302 of the viewer screen 300 (see FIG. 7). An image of a specific frame of the post-treatment moving image 2, for example, the final frame therein, is displayed in the pre-treatment image display region 322. For example, the moving image 1 is played when the play icon 334 of the pre-treatment image display region 322 is operated. During playback of the moving image 1, if the pause icon 336 is operated then playback of the moving image 1 is stopped, and if the play icon 334 is then operated, playback of the moving image 1 is resumed from the stopped location. During playback of the moving image 1, if the stop icon 332 is operated then playback of the moving image 1 is stopped, and if the play icon 334 is then operated, the moving image 1 is played from the start. When the repeat icon 338 is operated, playback of the moving image 1 is repeated from the start. Playback of the moving image 2 is similar to playback of the moving image 1.

In order to confirm the efficacy of treatment, the user (ophthalmologist or the like) specifies the analysis points in the image in the pre-treatment image display region 322 or the post-treatment image display region 324 via the input/instruction device 174 of the image viewer 150. In FIG. 7 three analysis points from analysis point 1 to analysis point 3 have been specified. The analysis points may be specified in the image in either the pre-treatment image display region 322 or the post-treatment image display region 324. For example, when an analysis point is specified in the pre-treatment image display region 322, a square box is displayed on the pre-treatment image display region 322 so as to surround the specified location. Furthermore in the post-treatment image display region 324, a square box is also displayed on the post-treatment image display region 324 so as to surround a location corresponding to the specified location in the pre-treatment image display region 322.

When the analysis points (1 to 3) have been specified as described above, at step 236 the image viewer 150 transmits data such as coordinates indicating the positions of the analysis points to the management server 140.

The management server 140 to which the data of the analysis points has been transmitted then, at step 238, executes analysis processing, described in detail later. At step 240, the management server 140 that has executed the analysis processing transmits image data for a display screen displaying analysis results and the moving image data of the moving images 1, 2 to the image viewer 150.

The image viewer 150 that has received the image data and the moving image data displays the viewer screen (analysis result display screen) 300 (see FIG. 8) on the display 172. The viewer screen (analysis result display screen) 300 (see FIG. 8) is described later.

Next, explanation follows regarding the analysis processing. The management server 140 instructed by the ophthalmic device 110 to perform analysis processing as described above executes the analysis processing program. The analysis processing method illustrated in the flowchart of FIG. 6 is implemented by the CPU 162 of the management server 140 executing the analysis processing program.

Figure 6:
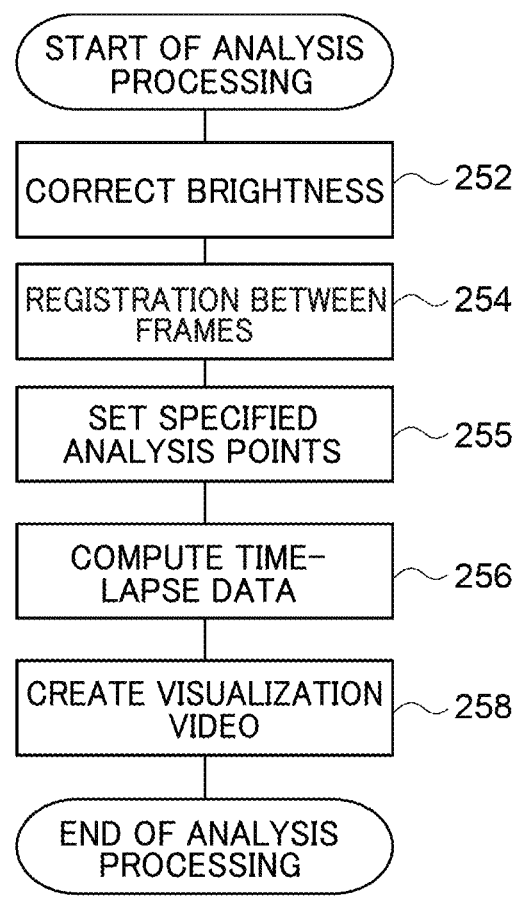
FIG. 6 is a flowchart for an analysis processing program.

At step 252 in FIG. 6, the image processing section 182 corrects a brightness value of each pixel in the respective images of the N×T frames of moving image 1 and moving image 2 read as described above such that, for example, the respective contrasts thereof are brought within a specific range, for example so as to match each other.

More specifically, the effects of fluctuations in the background brightness are eliminated in the following manner. Namely, the image processing section 182 may compute an average brightness for each frame, and divide each of the pixel values for a given frame by the average brightness of that frame to remove background brightness. Alternatively, the background brightness may be removed by performing processing to divide a signal value for each pixel by an average value of a peripheral range of fixed width around the corresponding pixel in each frame. The image processing section 182 also removes the effects of background brightness in a similar manner for all other frames. Similar processing is executed for both the moving image 1 and the moving image 2.

At step 254, the image processing section 182 executes registration of the fundus image positions between chronologically preceding and following frames in the N×T frames in the moving image 1 and moving image 2 respectively. For example, the image processing section 182 selects one specific frame from out of the N×T frames in either moving image 1 or moving image 2, moving image 1 in this example, as a reference frame. The reference frame selected is preferably a frame after a certain passage of time and subsequent to the start of sufficient ICG perfusion through the arteries and veins. This is because large fluctuations in the locations of the captured blood vessels and in the signal strength of frames occur immediately after injection of ICG. The image processing section 182 performs registration using a method such as cross-correlation processing using the brightness values of the pixels in the frames so as to align a feature point in the fundus region of a specific frame with this feature point in the fundus region of the reference frame. The image processing section 182 performs similar registration to the reference frame for positions in all of the other frames. The image processing section 182 executes similar registration processing for both the moving image 1 and the moving image 2. Note that the image processing section 182 may also perform correction of positional misalignment (registration error) between the frames of moving image 1 and moving image 2 so as to align the feature points in all the frames of moving image 1 and moving image 2.

At step 255, the processing section 186 sets the analysis points as determined by the coordinate data of the analysis points specified by the user (ophthalmologist or the like) and transmitted from the management server 140.

At step 256, the processing section 186 computes time-lapse data for each analysis point.

Explanation follows regarding the time-lapse data. The time-lapse data is data derived from plural pixel values of the pixels of the analysis points or of a region including the analysis points, and is acquired from each of the frames configuring the moving images. Examples of such time-lapse data include brightness values, brightness change rate, saturation rate, this being the brightness as a proportion of a maximum brightness value, blood flow velocity, and the like. This data is either acquired or computed for all of the frames configuring moving image 1 and moving image 2.

The brightness values are acquired from the pixel values at the analysis points in each frame image of the fundus images that have been processed at steps 252, 254.

The brightness change rate is obtained by computing for moving image 1 and moving image 2 brightness differences between the analysis points in chronologically preceding and following frame images.

The saturation rate is obtained by extracting a maximum brightness value of the brightness at each of the analysis points in each frame image, and computing this as a proportion of the maximum brightness value out of the brightness at each of the other analysis points.

The blood flow velocity can be acquired using adaptive optics scanning laser ophthalmoscopy (AOSLO), not illustrated in the drawings, to measure the movement velocity of structures (for example red blood cells) floating through the blood vessels at the analysis points.

At step 258, the display control section 184 creates a visualization moving image in which the time-lapse data is represented in color. This is more specifically performed in the following manner.

Colors corresponding to pixel brightness value magnitudes are assigned in advance. This allocation to brightness values may be allocation performed in a range between a minimum brightness value and a maximum brightness value across all frames and all pixels. In order to define a practical pixel value range from which the pixel values of abnormal points such as bright dots and dark dots have been removed, all pixel values in each of the images may be sorted, with the allocation then being performed between a minimum brightness value and a maximum brightness value respectively defined as the second percentile and ninety-eighth percentile in a histogram of the pixel values obtained thereby.

The colors may be allocated to the brightness values between the minimum brightness value and the maximum brightness value by allocating colors of various hues including green and the like according to their sequence in the visible light spectrum between two contrasting colors (for example blue and red).

Note colors may be allocated in a manner that does not add colors of other hues between two contrasting colors. For example, in a case in which blue and red are selected as the two contrasting colors, a pure blue may be allocated to the minimum brightness value, a pure red may be allocated to the maximum brightness value, and color allocation may be performed by gradually introducing red to the pure blue on progression from the minimum brightness value toward the maximum brightness value. Alternatively, in a case in which blue and green are selected as the two contrasting colors, a pure blue may be allocated to the minimum brightness value, a pure green may be allocated to the maximum brightness value, and color allocation may be performed by gradually introducing green to the pure blue on progression from the minimum brightness value toward the maximum brightness value.

For the brightness change of each pixel between frames, blue may be allocated to a maximum change value on the minus side, green (dead center) may be allocated when the change value is 0 (cases in which there is no change), and red may be allocated to a maximum change value on the plus side. Intermediate colors between blue and green and between green and red (colors assigned according to their sequence between blue and green and between green and red in visible light) may respectively be allocated to change values from the maximum change value to 0 and from 0 to the maximum plus side change value. The display control section 184 may first, for each of moving image 1 and moving image 2, calculate the brightness change values of the pixels in each frame image by calculating the differences of the brightness values of the respective pixels of a given frame image with respect to the corresponding pixels in the frame one previous to the given frame. The display control section 184 creates second color moving images from the moving image 1 and the moving image 2 by allocating the colors corresponding to the pixel brightness change values to the respective pixels in each frame image.

For the saturation rate, this being the brightness of each pixel in each frame image as a proportion of the maximum brightness value, red is allocated to a saturation rate of 100%, blue is allocated to a saturation rate of 0%, and intermediate colors between blue and red (colors assigned according to their sequence between blue and red in visible light) are allocated to saturation rates lying between the saturation rates of 100% and 0%. The display control section 184 calculates the saturation rate for each of the pixels of each frame image for moving image 1 and moving image 2, and creates third color moving images from the moving image 1 and the moving image 2 by allocating the colors corresponding to the saturation rates to the respective pixels in each frame image.

For the blood flow velocity through the blood vessels of the fundus in each frame, red is allocated to the highest velocity, blue is allocated to the lowest velocity, and intermediate colors between blue and red are allocated to velocities between the highest velocity and the lowest velocity (colors assigned according to their sequence between blue and red in visible light). The display control section 184 creates fourth color moving images from the moving image 1 and the moving image 2 by allocating the colors corresponding to the velocity to the respective pixels in each frame image.

The user (ophthalmologist or the like) checks the time-lapse data at the analysis points to confirm the efficacy of treatment. For example, the user (ophthalmologist or the like) operates the brightness information display instruction icon 312. When the brightness information display instruction icon 312 is operated, as illustrated in FIG. 8, brightness value graphs 374, 378, 382 are displayed in the information display region 306 corresponding to numbers of the respective analysis points 1 to 3 displayed in number display regions 372, 376, 380. In the brightness value graphs 374, 378, 382, brightness values are represented on the vertical axis, and elapsed time since ICG injection (more specifically from the input time of the imaging start instruction at steps 204, 214) is represented on the horizontal axis, with pre-treatment and post-treatment brightness values displayed on the graphs for each of the analysis points. The pre-treatment brightness values are displayed using dotted lines, and the post-treatment brightness values are displayed using solid lines. The brightness value graphs are examples of comparative images.

The analysis points that the user (ophthalmologist or the like) has specified in order to confirm the efficacy of treatment are pathological lesions where PDT is performed. The velocity of blood fluid flowing through the blood vessels at such pathological lesions is comparatively low. When PDT is performed and this treatment is effective, then the velocity of blood fluid flowing through the blood vessels at the pathological lesions will show a comparative increase. Thus when the ICG administered by intravenous injection begins to reach the pathological lesion, light of the near-infrared fluorescence wavelength emitted from the ICG is captured, and the brightness values of the pixels corresponding to the pathological lesion change according to the blood flow velocity. The more effective the treatment, the higher the velocity of the ICG flowing through the blood vessels of the pathological lesion will becomes, resulting in a sharper spike in brightness values and a greater difference in shape between the pre-treatment and post-treatment brightness value graphs. The extent of the change in shape between the pre-treatment and post-treatment brightness value graphs enables the efficacy of the treatment to be ascertained.

More specifically, at the analysis point 1, the shape is somewhat different between the pre-treatment and post-treatment brightness value graphs, and so this enables determination that the treatment at analysis point 1 has been somewhat effective. However, there is no significant change in the shape between the pre-treatment and post-treatment brightness value graphs at the analysis point 2, and so this enables determination that the treatment has not been effective at analysis point 2. On the other hand, there is a comparatively large difference between the shapes of the pre-treatment and post-treatment brightness value graphs at the analysis point 3, and so this enables determination that the treatment has had comparatively high efficacy at analysis point 3.

Moreover, when the brightness information display instruction icon is operated, not only are the brightness value graphs 374, 378, 382 displayed in the information display region 306 as described above, but the first color moving images are also played in the pre-treatment image display region 322 and the post-treatment image display region 324 according to operation of the icons from the stop icon 332 to the repeat icon 338.

Thus the information display region 306 configured in this manner presents a visualization of the velocity of blood fluid flowing through the blood vessels at the analysis points before and after treatment using the pre-treatment and post-treatment brightness value graphs 374, 378, 382, thereby enabling the doctor to ascertain the efficacy of treatment. Moreover, a visualization of the manner in which the blood fluid flows through the blood vessels at the fundus of the examined eye is presented by the first color moving images in the pre-treatment image display region 322 and the post-treatment image display region 324.

Moreover, when the brightness change information display instruction icon 314 is operated, respective graphs of the change in brightness values before and after treatment are displayed in the information display region 306 corresponding to the numbers of the analysis points 1 to 3 displayed in the number display regions 372, 376, 380. The second color moving images are played in the pre-treatment image display region 322 and the post-treatment image display region 324 according to operation of the icons from the stop icon 332 to the repeat icon 338.

The information display region 306 configured in this manner presents a visualization of the velocity of blood fluid flowing through the blood vessels at the analysis points before and after treatment using the graphs of change in the brightness values before and after treatment, thereby enabling the doctor to ascertain the efficacy of treatment. Moreover, a visualization of the manner in which the blood fluid flows through the blood vessels at the fundus of the examined eye is presented by the second color moving images in the pre-treatment image display region 322 and the post-treatment image display region 324.

Moreover, when the saturation rate display instruction icon 316 is operated, graphs of the change in saturation rate between before and after treatment are displayed in the information display region 306 corresponding to the numbers of the analysis points 1 to 3 displayed in the number display regions 372, 376, 380. The third color moving images are played in the pre-treatment image display region 322 and the post-treatment image display region 324 according to operation of the icons from the stop icon 332 to the repeat icon 338.

The information display region 306 configured in this manner presents a Visualization of the velocity of blood fluid flowing through the blood vessels at the analysis points before and after treatment using the graphs of change in the saturation rate before and after treatment, thereby enabling the doctor to ascertain the efficacy of treatment. Moreover, a visualization of the velocity of the blood fluid flowing through the blood vessels at the fundus of the examined eye is presented by the third color moving images in the pre-treatment image display region 322 and the post-treatment image display region 324.

Furthermore, when the velocity display instruction icon 318 is operated, graphs of the change in velocity before and after treatment are displayed in the information display region 306 corresponding to the numbers of the analysis points 1 to 3 displayed in the number display regions 372, 376, 380. The fourth color moving images are played in the pre-treatment image display region 322 and the post-treatment image display region 324 according to operation of the icons from the stop icon 332 to the repeat icon 338.

The information display region 306 configured in this manner presents a visualization of the velocity of blood fluid flowing through the blood vessels at the analysis points before and after treatment using the graphs of change in the blood flow velocity before and after treatment, thereby enabling the doctor to ascertain the efficacy of treatment. Moreover, a visualization of the manner in which the blood fluid flows through the blood vessels at the fundus of the examined eye is presented by the fourth color moving images in the pre-treatment image display region 322 and the post-treatment image display region 324.

In the present exemplary embodiment described above, data to create a visualization of the state of the blood fluid flowing through the blood vessels at the analysis points is computed, and a visualization of the state of the blood fluid flowing through the blood vessels at the analysis points is created based on the computed data.

Next, explanation follows regarding various modified examples of the technology disclosed herein.

First Modified Example

Although the time-lapse data is computed from each of the pixel values in the entirety of the frame images of moving images 1, 2 in the exemplary embodiment described above, a configuration may be adopted in which time-lapse data is computed for each of the pixel values in a specific region that includes a pathological lesion and is smaller than the entire image in order to create the first color moving image to the fourth color moving image. Adopting such an approach enables a reduction in calculation processing to be achieved.

Second Modified Example

Although in the exemplary embodiment described above the moving images 1, 2 are acquired before and after a single treatment session, a configuration may be adopted in which moving images are acquired before and after each of plural treatment sessions, with the analysis processing executed using the moving images from before and after each treatment so as to display the outcomes.

Third Modified Example

Although in the exemplary embodiment described above the analysis points are specified individually by the doctor, a configuration may be adopted in which blood vessels at pathological lesions are automatically selected as analysis points after first identifying a pathological lesion.

Moreover, instead of a doctor selecting the analysis points individually, the analysis points may be specified automatically using an artificial intelligence (AI) on the management server 140. FIG. 9 illustrates operation of an ophthalmic system 100 by a doctor before and after treatment in cases in which the analysis points are specified automatically by an AI. In the operation of FIG. 9, the same reference numerals are appended to elements of operation similar to those in FIG. 5, and explanation thereof is omitted.

As illustrated in FIG. 9, after the moving images 1, 2 have been read at step 226, the management server 140 executes the analysis processing of step 238, executes the viewer screen creation of step 228, and executes transmission of the image data and moving image data of moving images 1, 2 of 240.

Steps 252 to 258 in FIG. 6 are executed during the analysis processing of step 238 in FIG. 9. However, at the processing of step 255, an AI employs feature points on the choroidal blood vessels and information about the position of the PDT treatment region to automatically set feature points on choroidal blood vessels in the PDT treatment region (for example at branch points) as the analysis points.

Fourth Modified Example

In the exemplary embodiment described above, a visualization of the velocity of blood fluid flowing through the blood vessels at the analysis points before and after treatment is presented using the graphs of the time-lapse data from before and after treatment. The following processing may also be performed in the technology disclosed herein. For example, a relationship between a treatment efficacy level and a measure of the change in shape of the graphs of the time-lapse data from before and after treatment may be determined in advance and stored in the memory 164 of the management server 140. The management server 140 calculates the measure of change in shape of the graphs of the time-lapse data from before treatment and after treatment, then determines the treatment efficacy level corresponding to the measure of change based on the above relationship to the calculated measure of change, and transmits the determined treatment efficacy level to the image viewer 150. The image viewer 150 displays the treatment efficacy level on the display 172 of the image viewer 150.

Fifth Modified Example

In the exemplary embodiment described above an example has been described in which a fundus image is acquired by the ophthalmic device 110 with an internal light illumination angle of about 200 degrees. However, the technology disclosed herein is not limited thereto, and the technology disclosed herein may, for example, be applied even when the fundus image imaged by an ophthalmic device has an internal illumination angle of 100 degrees or less.

Sixth Modified Example

In the exemplary embodiment described above the ophthalmic device 110 uses SLO to image an ICG moving image. However, the technology disclosed herein is not limited thereto, and for example an ICG moving imaged with a fundus camera may be employed.

Seventh Modified Example

In the exemplary embodiment described above the management server 140 executes the analysis processing program. However, the technology disclosed herein is not limited thereto. For example, the ophthalmic device 110 or the image viewer 150 may execute the analysis processing program.

Eighth Modified Example

The exemplary embodiment described above describes an example of the ophthalmic system 100 equipped with the ophthalmic device 110, the photodynamic therapy system 120, the management server 140, and the image viewer 150; however the technology disclosed herein is not limited thereto. For example, as a first example, the photodynamic therapy system 120 may be omitted, and the ophthalmic device 110 may be configured so as to further include the functionality of the photodynamic therapy system 120. Moreover, as a second example, the ophthalmic device 110 may be configured so as to further include the functionality of one or both of the management server 140 and the image viewer 150. For example, the management server 140 may be omitted in cases in which the ophthalmic device 110 includes the functionality of the management server 140. In such cases, the analysis processing program is executed by the ophthalmic device 110 or the image viewer 150. Moreover, the image viewer 150 may be omitted in cases in which the ophthalmic device 110 includes the functionality of the image viewer 150. As a third example, the management server 140 may be omitted, and the image viewer 150 may be configured so as to execute the functionality of the management server 140.

Ninth Modified Example

Although in the exemplary embodiment described above photodynamic therapy (PDT) is employed as the treatment, the technology disclosed herein is not limited thereto. The technology disclosed herein may be employed to confirm efficacy before and after treatment for various pathological changes related to the fundus, such as treatment by photocoagulation surgery, treatment by administration of anti-VEGF drugs, treatment by surgery on the vitreous body, and the like.

Other Modified Examples

The data processing described in the exemplary embodiment described above is merely an example thereof. Obviously, unnecessary steps may be omitted, new steps may be added, and the sequence of processing may be changed within a range not departing from the spirit thereof.

Moreover, although in the exemplary embodiment described above an example has been given of a case in which data processing is implemented by a software configuration utilizing a computer, the technology disclosed herein is not limited thereto. For example, instead of a software configuration utilizing a computer, the data processing may be executed solely by a hardware configuration of FPGAs or ASICs. Alternatively, a portion of processing in the data processing may be executed by a software configuration, and the remaining processing may be executed by a hardware configuration.

What is claimed is:

1. An image processing method comprising:
   performing a first registration of a first fundus region in a plurality of first frames in a first moving image of a subject eye;
   performing a second registration of a second fundus region in a plurality of second frames in a second moving image of the subject eye, the first moving image being associated with a first imaging scan taken at a first time and the second moving image of the subject's eye being a different moving image than the first moving image and being associated with a second imaging scan taken at a second time, the second imaging scan and second time being different from the first imaging scan and first time, respectively;
   computing a first analysis data by performing a predetermined image processing of a first point in the first moving image after the first registration;
   computing a second analysis data by performing the predetermined image processing of a second point, which corresponds to the first point, in the second moving image after the second registration; and
   comparing the first analysis data and the second analysis data.

2. The image processing method of claim 1, wherein analyzing includes:
   computing first visualization data enabling visualization of a state of blood fluid flowing at the location including the first analysis point when imaging the first moving image; and
   computing second visualization data enabling visualization of a state of blood fluid flowing at the location including the second analysis point when imaging the second moving image.

3. The image processing method of claim 2, further comprising creating a comparative image to compare the first visualization data against the second visualization data.

4. The image processing method of claim 2, wherein:
   the first visualization data is computed based on a pixel value at the location including the first analysis point in each of the plurality of first frames; and
   the second visualization data is computed based on a pixel value at the location including the second analysis point in each of the plurality of second frames.

5. The image processing method of claim 2, wherein:
   the first visualization data includes values determined based on a pixel value of an image in each of the frames at respective timings in the first moving image; and
   the second visualization data includes values determined based on a pixel value of an image in each of the frames at respective timings in the second moving image.

6. The image processing method of claim 5, wherein:
   a first graph is created based on the first visualization data with the pixel values represented on a vertical axis and with the timings represented on a horizontal axis; and
   a second graph is created based on the second visualization data with the pixel values represented on a vertical axis and with the timings represented on a horizontal axis.

7. The image processing method of claim 6, wherein the first graph and the second graph are displayed superimposed.

8. The image processing method of claim 2, wherein:
   the first visualization data and the second visualization data include at least one out of a brightness value, a brightness change rate, a saturation rate that is brightness as a proportion of a maximum brightness value, or a blood flow velocity at the location including the first analysis point and the location including the second analysis point.

9. The image processing method of claim 1, further comprising:
   creating a first color moving image representing a change in pixel value at each pixel of an image in each of the frames of the first moving image; and
   creating a second color moving image representing a change in pixel value at each pixel of an image in each of the frames of the second moving image.

10. The image processing method of claim 1, wherein:
    performing the first registration of the first fundus region in the plurality of first frames in the first moving image is achieved by aligning a feature point in the first fundus region of the plurality of first frames in the first moving image; and
    performing the second registration of the second fundus region in the plurality of second frames in the second moving image is achieved by aligning a feature point in the second fundus region of the plurality of second frames in the second moving image.

11. The image processing method of claim 1, further comprising a correcting positional misalignment between each of the frames of the first moving image and each of the frames of the second moving image.

12. The image processing method of claim 1, wherein the first moving image and the second moving image are wide angled fundus images of an examined eye.

13. The image processing method of claim 1, wherein:
    the first moving image and the second moving image are moving images in which a choroidal blood vessel of an examined eye is imaged as the blood vessel; and
    the first analysis point and the second analysis point are points set on the choroidal blood vessel.

14. The image processing method of claim 1, further comprising:
    correcting a brightness value of each pixel in each of the frames of the first moving image such that a contrast is brought within a specific range; and
    correcting a brightness value of each pixel in each of the frames of the second moving image such that a contrast is brought within a specific range.

15. The image processing method of claim 1, wherein:
    the first analysis point is a feature point on a blood vessel that has been automatically selected by artificial intelligence.

16. The image processing method of claim 1, wherein:
    the first moving image and the second moving image are moving images imaged using fluorescent light.

17. The image processing method of claim 1, wherein the first moving image is a moving image imaged before treatment and the second moving image is a moving image imaged after treatment.

18. The image processing method of claim 1, wherein the second moving image has been imaged on an imaging date that is different from an imaging date of the first moving image.

19. A non-transitory computer-readable medium storing an information processing program that causes a computer to
- perform a first registration of a first fundus region in a plurality of first frames in a first moving image of a subject eye;
- perform a second registration of a second fundus region in a plurality of second frames in a second moving image of the subject eye, the first moving image being associated with a first imaging scan taken at a first time and the second moving image of the subject's eye being a different moving image than the first moving image and being associated with a second imaging scan taken at a second time, the second imaging scan and second time being different from the first imaging scan and first time, respectively;
- compute a first analysis data by performing a predetermined image processing of a first point in the first moving image after the first registration;
- compute a second analysis data by performing the predetermined image processing of a second point, which corresponds to the first point, in the second moving image after the second registration; and
- compare the first analysis data and the second analysis data.

20. The non-transitory computer-readable medium of claim 19, wherein the second moving image has been imaged on an imaging date that is different from an imaging date of the first moving image.

21. An image processing device comprising:
- a memory configured to store a program for causing an image processing method to be executed by a processor; and
- a processor configured to execute the image processing method by executing the program stored in the storage device, wherein the image processing method comprises;
- performing a first registration of a first fundus region in a plurality of first frames in a first moving image of a subject eye;
- performing a second registration of a second fundus region in a plurality of second frames in a second moving image of the subject eye, the first moving image being associated with a first imaging scan taken at a first time and the second moving image of the subject's eye being a different moving image than the first moving image and being associated with a second imaging scan taken at a second time, the second imaging scan and second time being different from the first imaging scan and first time, respectively;
- computing a first analysis data by performing a predetermined image processing of a first point in the first moving image after the first registration;
- computing a second analysis data by performing the predetermined image processing of a second point, which corresponds to the first point, in the second moving image after the second registration; and
- comparing the first analysis data and the second analysis data.

22. The image processing device of claim 21, wherein the second moving image has been imaged on an imaging date that is different from an imaging date of the first moving image.

* * * * *